(12) United States Patent
Iraneta et al.

(10) Patent No.: US 8,999,156 B2
(45) Date of Patent: Apr. 7, 2015

(54) FRIT FOR HIGH PRESSURE LIQUID CHROMATOGRAPHY

(75) Inventors: Pamela C. Iraneta, Brighton, MA (US);
Jon Belanger, Whitinsville, MA (US);
Raymond P. Fisk, Norton, MA (US)

(73) Assignee: Waters Technologies Corporation, Milford, MA (US)

( * ) Notice: Subject to any disclaimer, the term of this patent is extended or adjusted under 35 U.S.C. 154(b) by 2221 days.

(21) Appl. No.: 10/591,377

(22) PCT Filed: Mar. 4, 2005

(86) PCT No.: PCT/US2005/007152
§ 371 (c)(1),
(2), (4) Date: May 24, 2007

(87) PCT Pub. No.: WO2005/087340
PCT Pub. Date: Sep. 22, 2005

(65) Prior Publication Data
US 2007/0295663 A1 Dec. 27, 2007

Related U.S. Application Data

(60) Provisional application No. 60/550,993, filed on Mar. 5, 2004.

(51) Int. Cl.
*G01N 30/60* (2006.01)
(52) U.S. Cl.
CPC .................................. *G01N 30/603* (2013.01)
(58) Field of Classification Search
CPC .................................................... G01N 30/603
USPC ......... 210/510.1, 635, 656, 659, 198.2, 502.1
See application file for complete search history.

(56) References Cited

U.S. PATENT DOCUMENTS

| 4,039,703 A | 8/1977 | Kamijo | |
|---|---|---|---|
| 4,399,032 A * | 8/1983 | Mott | 210/198.2 |

(Continued)

FOREIGN PATENT DOCUMENTS

| JP | 63-20059 | 2/1988 |
|---|---|---|
| JP | 07260763 | 10/1995 |

(Continued)

OTHER PUBLICATIONS

PTO Translation No. 10-378177180 of Japan Patent No. 2004177180.*

(Continued)

*Primary Examiner* — Ernest G Therkorn
(74) *Attorney, Agent, or Firm* — Locke Lord LLP; Nicholas J. DiCeglie, Jr.; Brian S. Matross

(57) ABSTRACT

A frit (44) includes a porous support structure having a plurality of void spaces, where a plurality of secondary particles (46) are filled in the void spaces, the secondary particles (46) being dimensioned with respect to the void spaces such that the frit (44) retains packing materials with diameters of less than about 2.5 microns. Preferably one or more frits (44) are received in a high pressure liquid chromatography (HPLC) chromatographic column, where the column includes fittings and filter assemblies for receiving frits (44) at its inlet and outlet. The frit (44) can be constructed from a porous support structure with void spaces or pores that are filled with secondary particles (46) smaller those used to manufacture the support. The particles (46) contained in the void spaces are large enough to be retained by the support, but small enough to create a finer network of interconnected channels within the support's void spaces that are capable of retaining sub-2.5 micrometer particles.

21 Claims, 10 Drawing Sheets

(56) References Cited

U.S. PATENT DOCUMENTS

| | | | |
|---|---|---|---|
| 4,469,597 A * | 9/1984 | Mott | 210/198.2 |
| 4,613,369 A | 9/1986 | Koehler | |
| 4,719,011 A * | 1/1988 | Shalon et al. | 210/198.2 |
| 4,746,341 A | 5/1988 | Komoda | |
| 4,837,195 A * | 6/1989 | Cox et al. | 502/408 |
| 4,888,114 A | 12/1989 | Gaddis | |
| 4,966,696 A * | 10/1990 | Allington et al. | 210/198.2 |
| 4,976,760 A | 12/1990 | Helferich | |
| 5,114,447 A | 5/1992 | Davis | |
| 5,147,538 A * | 9/1992 | Wright et al. | 210/198.2 |
| 5,456,740 A | 10/1995 | Snow | |
| 5,925,156 A | 7/1999 | Motoki | |
| 5,985,140 A | 11/1999 | Dewaele et al. | |
| 6,080,219 A * | 6/2000 | Jha et al. | 55/486 |
| 2008/0272053 A1 * | 11/2008 | Chandler | 210/658 |

FOREIGN PATENT DOCUMENTS

| | | |
|---|---|---|
| JP | 2001-249120 | 9/2001 |
| JP | 2004-037266 | 2/2004 |
| JP | 2004/177180 | 6/2004 |
| WO | WO03/014450 A1 | 2/2003 |

OTHER PUBLICATIONS

PTO Translation No. 14/4166 of Japan Patent No. 63-020059 Jun. 2014.*
PTO Translation No. 14/4161 of Japan Patent No. 2001249120 Jun. 2014.*
PTO Translation No. 14/4172 of Japan Patent No. 2004037266 Jun. 2014.*
Written Opinion of the International Searching Authority issed in PCT/US05/07152 (May 20, 2005).
International Preliminary Report on Patentability for PCT/US2005/007152 (Sep. 5, 2006).
English Language Abstract of Japanese Application No. JP2004/177180 (1 page).
GB Examination Report (5 pages).
Notice of Rejection and English Language Translation of Notice of Rejection for corresponding Japanese Application No. 2007-502028 (Sep. 21, 2010).

* cited by examiner

Top of 0.5 media grade frit filled with 3.5 micrometer chromatographic particles.

Bottom or down stream side of 0.5 media grade frit filled with 3.5 micrometer chromatographic particles Top of 0.5 media grade frit filled with 2 micrometer chromatographic particles.

SEM of 0.5 media grade frit prior to filling

SEM of 0.5 media grade frit after filling with 4 micrometer spherical stainless steel particles and sintered in secondary process.

FRIT FOR HIGH PRESSURE LIQUID CHROMATOGRAPHY

This application is a U.S. national phase application, pursuant to 35 U.S.C. §371, of PCT international application Ser. No. PCT/US2005/07152, filed Mar. 4, 2005, designating the United States and published in English on Sep. 22, 2005 as publication WO 2005/087340 A1, which claims priority to U.S. provisional application Ser. No. 60/550,993, filed Mar. 5, 2004. The entire contents of the aforementioned patent applications are incorporated herein by this reference.

RELATED APPLICATION

This application claims priority to: U.S. provisional application Ser. No. 60/550,993, filed 05 Mar. 2004. The aforementioned application is incorporated herein in its entirety by this reference.

BACKGROUND OF INVENTION

The subject invention relates to frits configured for use in high pressure liquid chromatography (HPLC) chromatographic columns, and more particularly, to a frit capable of retaining sub-2.5 micrometer particles. The frits also can serve as in-line filters arranged upstream of chromatographic columns in HPLC systems. A high pressure liquid chromatography (HPLC) column is widely used for the separation and quantification of solutes in a liquid stream. A typical chromatographic system, as shown in FIG. 7, includes at least the following major components: a pump 70, an injector 72, a chromatographic column 74, a detector 76, and a computer 78 running software capable of data acquisition and processing. The pump 70 is used to propel a liquid stream through the injector, column, and detector. The injector 72 is operably connected to the pump 70 and permits the introduction of a small volume of a liquid sample into the liquid stream prior to its entering the column 74. Sample components are then separated as they migrate through the column by means of a variety of interactions between the solutes and the packing material contained therein. Upon exiting the column the individual components are detected by the detector 76, before being discarded. A signal from the detector 76 is then processed by a suitable computer software program in the computer 78 to provide a numerical value indicating the amount of solute detected.

Central to advances in the field of HPLC are advances in packing material technology and theory. The particle sizes of chromatographic packing materials used in HPLC columns have been decreasing over time. In the late 1960's, 30 micrometer packings were in use. By the early 1970's, packing technologies were developed to provide reproducible columns containing 10 micrometer packing materials. In the late 1970's, columns packed with 5 micrometer packings became commercially available. During the 1980's and 1990's, improvements in the purity and surface derivatizations of the packing materials further advanced the science. Presently, 3 micrometer packing materials are in common use. With the 1999 introduction of 2.5 micrometer packings by Waters Corporation of Milford, Mass., the trend clearly is toward packing materials with smaller particle sizes.

Sintered porous filters are widely used at the inlet and outlet of chromatographic columns for the retention of the particulate packing material in HPLC columns. Sintered filters are typically made by compacting particles having a controlled particle size distribution into a desired shape, and then sintering to form an interconnected network of pores within the filter. Filters commonly used for chromatographic purposes can be made from a variety of materials, such as stainless steel, titanium, polyetheretherketone (PEEK), or polyethylene. The majority of HPLC columns in use today are manufactured using 316 stainless steel filters, since this material provides a good balance of high strength, low cost, and corrosion resistance.

The grade, or nominal particle retention rating, of a chromatographic frit within an HPLC column is chosen on a case-by-case basis as a function of the particles to be contained within the column. Porous sintered stainless steel frits used in chromatographic columns containing 5 micron or 3 micron particles typically use 2.0 or 0.5 grade media frits, respectively. Media grades can be derived from a combination of air flow, porosity, and particle retention measurements, and do not necessarily equate to the actual pore size through the filter. Filters are available from several sources such as VICI (Valco Instrument Co.) of Houston, Tex.; Alltech Associates Inc. of Deerfield, Ill.; and Mott Corporation's Porous Metal Products of Farmington, Conn. Although such porous filters are capable of retaining particles as small as 2.5 micrometers in diameter under HPLC conditions, these filters have difficulty adequately retaining particles less than 2.5 microns in diameter.

The channels through conventional frits are significantly larger than the particles the frit is designed to retain. In use, the frits behave as depth filters, where retention is accomplished through particle-particle and particle-wall interactions that block the tortuous path of the channels. The particle retention efficiency of such filters varies with the flow rate, particle size, and concentration of the challenge fluid. Retention under a given set of conditions does not guarantee retention under various conditions encountered in HPLC.

Challenging a nominal 0.5 grade frit with solutions containing sub-2.5 micron packing material has been shown to produce a cloudy effluent downstream of the frit, which is evidence of particle breakthrough. FIG. 8 is an example of a 0.5 grade frit packed with 2.2 micron chromatographic packing material. The frit was inserted in an outlet fitting and placed in a chromatography column for about one hour prior to disassembly, at which time the outlet fitting and frit were removed from the column. FIG. 8 is a scanning electron micrograph of the downstream side of the frit, which indicates that the packing material migrated through the frit, as evidenced by the contamination of the downstream side of the frit with the packing material. In addition, during use, columns containing sub-2.5 micron packings configured with conventional frits produce very sharp intermittent spikes in the baseline of UV chromatograms, which is indicative of particle breakthrough. For example, FIG. 9 shows UV chromatograms of the elements of three (A-C) HPLC columns packed with 1.7 micron chromatographic packing materials, which included conventional 0.5 grade frits. The spikes in the chromatograms are a clear indication of migration of packing material through the conventional frits. Therefore, under the desired use conditions, complete particle retention is not achieved using conventional frits.

Adequate retention of the chromatographic packing material is imperative to the mechanical stability of the column and the integrity of the HPLC system. It is particularly important when separation conditions demand very high column efficiencies. In order to achieve high efficiency in a minimal amount of time, the smallest possible particle size packings are desirable. The HPLC system's extra column tubing volume must be minimized in order not to detract from the efficiency performance of the column. This requires the use of very small diameter connection tubing, which can be easily plugged by particles if they are not well retained within the HPLC column. Conventional frits do not adequately retain sub-2.5 micrometer packings.

Sintered porous metal filters capable of retaining small particulates are typically made by pressing or molding metal or metal alloy powders into a desired shape. The formed shape is then sintered at high temperatures to provide a consolidated porous object. These porous materials are manufactured for specific applications and have characteristics that are dependent on the size, shape, and type of powder, in addition to the compression and temperature used in the process. Presently, frits used in HPLC columns are produced using 45-100 micrometer irregularly shaped powders as starting materials. Sintering powders of sub-10 micrometer particulate size and of a spherical shape is difficult. The difficulty in handling compressed forms made from <10 micrometer spherical particle size powders is due to poor mechanical strength of the "green" form prior to sintering. The poor mechanical strength makes the green forms too unstable to withstand the handling and transfer required in the sintering process. In addition, green forms produced by compacting <10 micron spherical powders tend to shrink excessively upon sintering, resulting in the formation of cracks and channels in the final frit structure.

Retention of sub-2.5 micrometer particles requires a finer pore structure than exists in conventional HPLC frits. A solution to this problem can be to compress further the existing frit media to further close off the pores and narrow the channel openings. However, this solution has the disadvantage of decreasing porosity and hence reducing permeability of the frit. Alternatively, smaller particle size powders can be used, but such powders suffer from poor "green" strength and excessive shrinkage during sintering. A number of patents propose ways to deal with this problem, frequently encountered in the filtration of gases for the semiconductor industry. In all cases a mechanically stable support is used to provide the needed strength either by layering on (U.S. Pat. Nos. 5,456,740; 4,746,341; 4,976,760; 4,039,703; and 5,925,156) or filling in the support (U.S. Pat. Nos. 5,114,447; 4,613,369; 4,888,114; and 6,080,219).

The subject invention overcomes the problems associated with conventional frits by providing a frit capable of retaining sub-2.5 micrometer packing materials, an HPLC system incorporating the frit, and a method of retaining sub-2.5 micrometer packing materials in HPLC columns.

SUMMARY OF THE INVENTION

A frit according to the subject invention includes a porous support structure having a plurality of void spaces, where a plurality of secondary particles are filled in the void spaces, the secondary particles being dimensioned with respect to the void spaces such that the frit retains packing materials with diameters of less than about 2.5 microns. In certain embodiments the void spaces are filled with the secondary particles such that the frit has a density of at least 50%. In particular, the frit of the subject invention can be configured for use in a chromatography system. Preferably the chromatography system is a high pressure liquid chromatography (HPLC) system. The frit can be arranged at either end of an HPLC column, or as an inline filter in the HPLC system preferably located upstream of the HPLC column.

As used herein, the term "frit" refers to any porous structure having a plurality of void spaces capable of retaining chromatographic particles. Encompassed in this definition is any number of known structures that are typically referred to as frits, filters, or screens.

A chromatography column according to the subject invention includes a tubular chamber having first and second ends, the tubular chamber being filled with a chromatographic packing material, and at least one frit received in the first and second ends.

The subject invention also is directed to a method of preparing a frit for use in a high pressure liquid chromatography column, including steps of: providing a porous support structure having a plurality of void spaces, and filling the void spaces with secondary particles, where the secondary particles are dimensioned with respect to the void spaces such that the frit retains chromatographic packing materials with particle diameters of less than about 2.5 microns. The method can include filling the void spaces with the secondary particles, such that the frit has a density of at least 50%. The method can further include a step of sintering the porous support structure and secondary particles to immobilize the secondary particles in the void spaces.

The subject invention further is directed to a method of preparing a frit for use in a high pressure liquid chromatography column, including steps of: providing a porous support structure having a plurality of void spaces, filling the void spaces with secondary particles, and orienting the porous support structure such that the secondary particles remain immobilized in the void spaces during use, where the secondary particles are dimensioned with respect to the void spaces such that the frit retains chromatographic packing materials with particle diameters of less than about 2.5 microns.

A chromatographic system for separating and quantifying solutes in a liquid stream, according to the subject invention, preferably includes a tubular chamber having first and second ends, the tubular chamber being filled with chromatographic packing materials; at least one frit received in the first and second ends of the tubular chamber, the frit having a porous support structure with a plurality of void spaces filled with a plurality of secondary particles dimensioned with respect to the void spaces such that the frit retains chromatographic packing materials with particle diameters of less than about 2.5 microns; a pump for propelling the liquid stream through the tubular chamber, the liquid stream contacting the chromatographic packing materials in the tubular chamber; an injector for delivery a sample into the liquid stream; and a detector for detecting individual components of the liquid stream as the liquid stream exits the second end of the tubular chamber.

The subject invention also encompasses a method for separating and quantifying solutes in a liquid stream, including steps of: providing a tubular chamber having first and second ends, the tubular chamber being filled with chromatographic packing materials; inserting at least one frit in the first and second ends of the tubular chamber, the frit having a porous support structure with a plurality of void spaces and a plurality of secondary particles dimensioned with respect to the void spaces such that the frit retains chromatographic packing materials with particle diameters of less than about 2.5 microns; propelling the liquid stream through the tubular chamber, the liquid stream contacting the chromatographic packing materials in the tubular chamber; injecting a sample into the liquid stream; and detecting individual components of the liquid stream as the liquid stream exits the second end of the tubular chamber.

According to the subject invention, a kit is provided for use with a high pressure liquid chromatography column, the column having a chamber with first and second ends. The kit includes: a fitting for threaded attachment to one of the first and second ends of the chamber and at least one frit received in the fitting, the frit having a porous support structure with a plurality of void spaces and a plurality of secondary particles, where the void spaces are filled with the plurality of secondary particles dimensioned with respect to the void spaces such that the frit retains chromatographic packing materials with particle diameters of less than about 2.5 microns, and instructions for use.

Preferably a frit according to the subject invention can receive the secondary particles in void spaces, where the void spaces are partially or completely filled with the secondary particles. The secondary particles can form within the void spaces a secondary pore network having a pore size that is capable of retaining chromatographic packing materials with diameters of less than about 2.5 microns.

According to the subject invention, the frit includes a porous support structure having a plurality of void spaces, the void spaces being filled with a plurality of secondary particles, such that the frit has a density of at least 50%. In other words, the porous support structure and secondary particles make up at least 50% by volume of the frit, whereby the frit forms a highly dense structure (greater than 50% dense). The highly dense structure of the frit enhances part strength and allows the frit to be press fit into cavities or columns without damaging the frit. In certain embodiments, the void spaces are filled with the secondary particles such that the depth of penetration in the frit by the secondary particles is greater than about 10 microns, more preferably ranging from about 28 microns to about 178 microns.

Preferably void spaces of the porous support structure are filled with the secondary particles and then sintered according to one preferred embodiment of the subject invention. By undergoing a sintering process, the porous support structure is heated, thereby immobilizing the secondary particles that fill the void spaces. The secondary particles can be sintered to each other, to the porous support structure surrounding the void spaces, or both. After sintering, the frit can be press fit in the tubular chamber of the HPLC column.

Alternatively, the frit can be configured as an in-line filter. For example, an in-line filter can be arranged upstream of the tubular chamber in an HPLC system, preferably between the pump and injector, or between the injector and tubular chamber.

According to another preferred embodiment of the invention, the frit is preferably is not sintered, but instead is oriented with respect to a flow direction through a tubular chamber. The frit preferably includes a porous support structure having a plurality of void spaces, the void spaces being filled with a plurality of secondary particles so as to retain chromatographic packing materials, where the secondary particles are dimensioned with respect to the void spaces and the packing materials such that the frit retains the packing materials with diameters of less than about 2.5 microns. In the present embodiment, because the frit is appropriately oriented relative to the flow direction of chromatographic packing materials, no sintering process is required. In particular, the frit can be arranged at the end of a tubular chamber and oriented with respect to a flow direction through the tubular chamber. Alternatively, the frit can be configured as an in-line filter. For example, an in-line filter can be arranged between the pump and injector or between the injector and tubular chamber of an HPLC system.

According to the above embodiments, and other embodiments falling within the scope of the subject invention, the frit preferably includes a porous support structure made from a material selected from the group of metals, metal alloys, metal oxides, ceramics, and polymers. In certain embodiments, the porous support structure preferably is made from a material selected from the group of sinterable metals, sinterable metal alloys, sinterable metal oxides, sinterable ceramics, and sinterable polymers. Also in certain embodiments, the porous support structure is made from a material selected from the group of stainless steel, titanium, PEEK, polyethylene, metal alloys (e.q., metal alloys available under the HASTELLOY® trademark from Haynes International, Inc. of Kokomo, Ind.), polypropylene, synthetic resinous fluorine-containing polymers (e.q., synthetic resinous fluorine-containing polymers available under the TEFLON® trademark from E.I. Du Pont de Nemours and Company of Wilmington, Del.), glass, silica, titania, and zirconia. A particularly preferred material for the porous support structure is stainless steel, more particularly 316 stainless steel.

According to the above embodiments, and other embodiments falling within the scope of the subject invention, the frit includes a support structure having a media grade ranging from about 0.5 to about 10, such as 0.5 media grade stainless steel or 2.0 media grade stainless steel. Secondary particles suitable to be filled in the void spaces of the support structure preferably are about 5 microns in diameter or smaller. More preferably, the secondary particles range from about 3 microns to about 5 microns in diameter. For example, secondary particles that are about 3.5 microns or 4 microns in diameter are suitable. One example of a suitable combination is a porous support structure made of 0.5 media grade sintered stainless steel filled with secondary particles of about 4 microns in diameter. Another example utilizes a porous support structure of 2.0 media grade sintered stainless steel filled with secondary particles of about 4 microns in diameter. In certain embodiments, the secondary particles can have the same composition as packing materials retained by the frit. Alternatively, the secondary particles can have a different composition than the packing materials. The secondary particles can have the same or a different composition than the porous support structure. In some embodiments, the secondary particles can be spherical stainless steel particles.

According to the above embodiments, and other embodiments falling within the scope of the invention, the packing materials retained by the frit are chromatographic packing materials. The chromatographic packing materials can be selected from the group of silica gel, derivatized silica gel, zirconia, derivatized zirconia, titanium oxide, derivatized titanium oxide, organo-silica hybrids, derivatized organo-silica hybrids, hybrids of metal oxides, and derivatized hybrids of metal oxides.

The chromatography column of the subject invention can be provided with a fitting connected to at least one end of a tubular chamber, the tubular chamber being filled with chromatographic packing material. Preferably, inlet and outlet fittings are provided at first and second ends of the chamber, respectively. In one embodiment, each fitting is provided with a sealing ring configured to receive a frit, and the frit is press fit into the fitting. Alternatively, in another embodiment, the inlet and outlet fittings are provided without sealing rings, and each frit can be press fit directly into a corresponding fitting. Each fitting can be provided with a cavity for receiving the frit, where the frit and fitting preferably engage in a sealing manner in the column. Alternatively, in a further embodiment, the frits can be press fit directly into the inlet and outlet ends of the chamber. A chromatography column according to the subject invention preferably can withstand pressures up to about 5,000 to 50,000 psi.

In certain embodiments, a first frit is arranged in a cavity of an inlet fitting, and a second frit is arranged in a cavity of the outlet fitting. Specifically, the first and second frits can be arranged with their top surfaces oriented toward the tubular chamber. In one example, each of the frits is received in a circular planar ring, and each corresponding ring and frit are configured to seal the inlet fitting and outlet fitting with the tubular chamber.

These and other unique features of the frit, in-line filter, chromatography column, methods, systems, and kit of the subject invention will become more readily apparent from the following description of the drawings taken in conjunction with the detailed description of the preferred embodiments.

BRIEF DESCRIPTION OF THE DRAWINGS

So that those having ordinary skill in the art to which the subject invention appertains will more readily understand how to construct and use a frit, in-line filter, and high pressure liquid chromatography column, method, and system of the subject invention, reference may be had to the drawings wherein.

Figure 1:
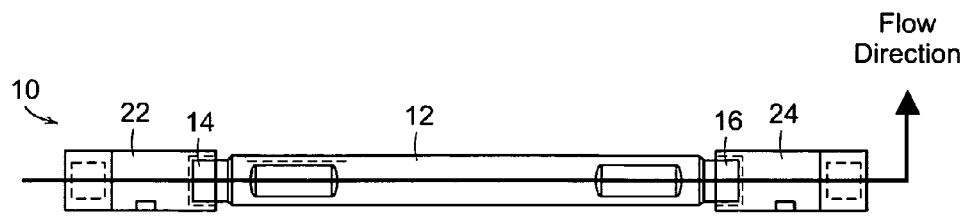
FIG. 1 is a partial cross-sectional view of a high pressure liquid chromatography (HPLC) column according to the subject invention, with a flow direction through the column indicated by the arrow.

These and other features of the frit, in-line filter, and high pressure liquid chromatography column, method, and system of the subject invention will become more readily apparent to those having ordinary skill in the art from the following detailed description of the preferred embodiments.

DETAILED DESCRIPTION OF CERTAIN PREFERRED EMBODIMENTS

In the description which follows, the term "frit" refers to any porous structure having a plurality of void spaces capable of retaining chromatographic particles. Encompassed in this definition is any number of known structures that are typically referred to as frits, filters, or screens.

A frit according to the subject invention is configured for use in a chromatography system, in particular, a high pressure liquid chromatography (HPLC) system. The frit can be arranged at either or both ends of a chromatography column (also referred to as an "HPLC column"). Alternatively, the frit can be used as an in-line filter, suitable for trapping and removing particulate contaminants from the fluid stream in an HPLC system. Preferably the frit is arranged at some location in the HPLC system upstream of the chromatography column. For example, the frit can be positioned upstream of the HPLC column, preferably between the pump and the injector, or between the injector and the chromatography column.

A frit according to the subject invention should be capable of retaining particles that are less than about 2.5 microns in diameter. The frit preferably includes a porous support structure having a plurality of pores or void spaces, where a plurality of secondary particles are filled in the void spaces, the secondary particles being dimensioned with respect to the void spaces such that the frit retains packing materials with diameters of less than about 2.5 microns. The void spaces are either partially or completely filled with the secondary particles, the particles being sufficiently small so as to enter and pack into the void spaces within the porous support structure, thereby producing a secondary pore network between the secondary particles, where the size of the secondary pore network is sufficiently small as to adequately retain packing materials of less than about 2.5 microns in diameter. In a preferred embodiment, the void spaces are filled with the secondary particles such that the frit has a density of at least 50%. In an HPLC column, the packing materials are chromatographic packing materials, and the frit should be capable of retaining chromatographic packing materials of less than about 2.5 microns in diameter.

Porous support structures of different grades, or nominal particle retention ratings, are commercially available. Such porous support structures can be designed for use in an HPLC column or other liquid or gas chromatography applications. Those of ordinary skill in the art will recognize that porous support structures are also known as chromatographic frits or filters. As used herein, the term "porous support structure" refers to any of a number of porous support structures, e.g., chromatographic frits or filters, that preferably have grades or particle retention ratings suitable for use in HPLC, either in chromatographic columns or as in-line filters. These porous support structures typically have nominal porosity and pore size grades, and are capable of retaining particles greater than about 2.5 microns in diameter. Porous support structures that are suitable for making frits according to the subject invention include porous sintered stainless steel porous support structures with grades ranging from about 0.5 to about 10, for example, 0.5 and 2.0 grade stainless steel porous support structures. The porous support structures can be made from particles that are compacted and sintered according to techniques known in the art, thereby producing structures with the specified grades.

The secondary particles used to form the secondary pore network in the porous support structure can be made of the same material as the porous support structure, or may have a different composition. Also, the secondary particles can have the same composition as chromatographic packing materials used in the HPLC column, or may have a different composition. The secondary particles can be irregularly shaped or spherical, and can be either narrowly sized or polydisperse. Preferably the secondary particles are spherical and narrowly sized, so as to aid in easy and efficient filling of the void spaces within the porous support structure, and to maximize open space within the newly formed secondary pore network.

In one preferred embodiment of the subject invention, once introduced into the void spaces of the porous support structure, the secondary particles are further immobilized in place to form a unified structure. To immobilize the secondary particles, a "second" heating or sintering step can be performed, where the second sintering step occurs after secondary particles are introduced into the void spaces of the porous support structure, in other words, after filling and compacting of the secondary particles in the porous support structure. The secondary particles can be sintered to each other, to the porous support structure, or both. As a result of sintering, the secondary particles are locked into place, thereby producing a unified structure having a secondary pore network formed within the porous support structure. Once formed, the final frit can be inserted into a chromatography column body directly, for example, by press fitting the frit into a sealing ring or inserting the frit into any number of typical column end fitting designs. Alternatively, the frit can be used as an in-line filter, and positioned anywhere in the HPLC system, preferably between the pump and injector, or between the injector and chromatography column.

In an example of the first preferred embodiment, the porous support structure is a 316 stainless steel sintered porous support structure with a nominal 2 micron rating, and the secondary particles are narrowly sized 4 micron spherical stainless steel particles, which are filled in the porous support structure to form a secondary pore network. The filled support structure is then sintered to form a unified structure. Because of the high surface area afforded by the much smaller secondary particles, during the secondary sintering step, the secondary particles will soften at a lower temperature than the coarser porous support structure, so that the size and shape of the porous support structure remains substantially unchanged.

According to a second preferred embodiment of the subject invention, the frit is arranged in a chromatography column and oriented with respect to the direction of flow through the column. In the second preferred embodiment, no sintering of the secondary particles is required. Instead, the secondary particles are filled in a porous support structure, and the frit is oriented in the direction of flow, so as to prevent fluid forces in the chromatography column from washing the secondary particles out of the porous support structure. Alternatively, an in-line filter constructed according to the second preferred embodiment could be oriented with respect to flow direction of a liquid stream upstream of the chromatography column, e.g., between the pump and injector, or between the injector and chromatography column.

In an example of the second preferred embodiment, the porous support structure is a 316 stainless steel sintered porous support structure with a nominal 2 micron rating, and the secondary particles are narrowly sized 4 micron stainless steel particles, which are filled in the porous support structure to form a secondary pore network. During filling, the secondary particles penetrate a surface of the porous support structure and then lodge within the porous support structure.

Those of ordinary skill in the art will recognize that a variety of combinations of porous support structures and secondary particles can be used. As described above, stainless steel and more specifically 316 stainless steel is a particularly preferred material for the porous support structure. In general, the porous support structure can be a material selected from the group of metals, metal alloys, metal oxides, ceramics, and polymers. Especially for the first embodiment discussed above, the porous support structure can be selected from the group of sinterable metals, sinterable metal alloys, sinterable metal oxides, sinterable ceramics, and sinterable polymers. Preferred materials for the above-described embodiments include stainless steel, titanium, PEEK, polyethylene, metal alloys (e.q., metal alloys available under the HASTELLOY® trademark from Haynes International, Inc. of Kokomo, Ind.), polypropylene, synthetic resinous fluorine-containing polymers (e.q., synthetic resinous fluorine-containing polymers available under the TEFLON® trademark from E.I. Du Pont de Nemours and Company of Wilmington, Del.), glass, silica, titania, and zirconia.

The porous support structure used to produce the frit of the subject invention preferably has a media grade ranging from about 0.5 to about 10. Examples include porous support structures made of 0.5 media grade sintered stainless steel, and 2.0 media grade sintered stainless steel. Preferably, the secondary particles filled in these support structures are about 5 microns in diameter or smaller. More particularly, the secondary particles range from about 3 microns to about 5 microns in diameter, for example 3.5 micron particles and 4 micron particles.

Once formed, the frits of the subject invention can be incorporated into any number of HPLC column end fittings that are intended to retain packing materials in a chromatographic column, the packing materials having particle diameters of less than about 2.5 microns. Since the size, shape, and mechanical properties of the final frits are similar to commercially available porous support structures, the frits of the subject invention can be substituted into HPLC columns generally without modification of existing designs. Examples of designs for arranging a frit at the end of a column include: press fitting into a sealing ring, crimp sealing into a filter housing, direct press fitting into an opening in the end of the column body, and direct press fitting into an opening in the column end fitting.

Referring now to the drawings wherein like reference numerals identify similar aspects of the subject invention, FIG. 1 illustrates a chromatography column 10 according to the subject invention, where the chromatography column can be used for high pressure liquid chromatography (HPLC). The chromatography column 10 preferably includes a tubular chamber 12 having first and second ends 14 and 16. The first end 14 of the chamber 12 is configured to receive at least one frit, and the second end 16 also is configured to receive at least one frit. The tubular chamber 12 preferably is externally threaded at the first and second ends 14 and 16 for receiving inlet and outlet fittings 22 and 24, respectively. The inlet fitting 22 and outlet fitting 24 are constructed in a similar manner, and each preferably includes internal threads for engagement with corresponding threads of the tubular chamber 12.

Figure 2A:
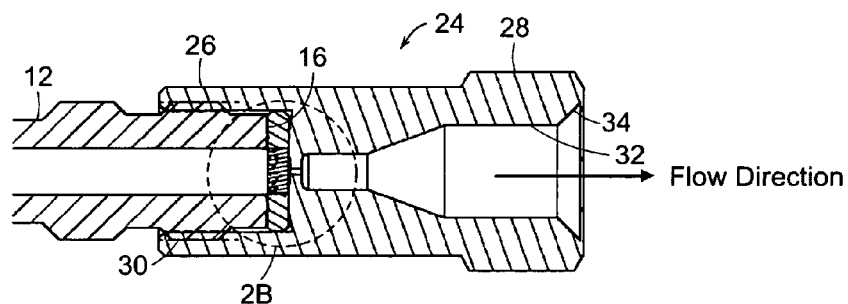
FIG. 2A is an enlarged cross-sectional view of a column outlet of the HPLC column of FIG. 1 according to one arrangement for holding the frit.
Figure 2B:
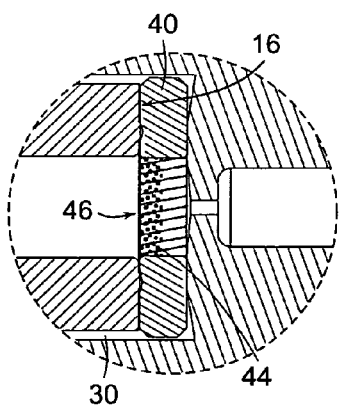
FIG. 2B is an enlargement of the area denoted in FIG. 2A.

FIG. 2A is an enlarged cross-sectional view of an end portion of the tubular chamber including a filter assembly, where both end portions of the chamber 12 are practically identical. In FIG. 2A, the second end 16 of the chamber 12 and outlet fitting 24 are depicted, although a similar arrangement is provided for the first end of the chamber and inlet fitting. FIG. 2B is a further enlargement showing details of the second end 16 of the chamber 12 and the outlet fitting 24.

As shown in FIG. 2A, the outlet fitting 24 includes first and second shafts 26 and 28. The first shaft 26 includes a first cavity 30 preferably having internal threads for receiving and cooperating with threads at or near the second end 16 of the chamber 12. The second shaft 28 includes a second cavity 32 preferably having internal threads for receiving and cooperating with threads of a compression screw and/or ferrule (not shown). Alternatively, the second cavity 32 can have a smooth internal finish or another finish for receiving other types of external attachment mechanisms. The cavity 32 preferably is shaped to be compatible with the type of attachment mechanism to be received therein, and can include a flared opening 34 to assist in guiding the attachment mechanism into the second cavity 32.

As shown in FIG. 2B, the second end 16 of the chamber 12 can include a circular planar ring 40 (or "sealing ring") having a hollow center :for receiving a frit 44 according to the subject invention. The circular planar ring 40 is in contact with the second end 16 of the chamber 12, the planar ring 40 being wedged between the second end 16 and an end of the cavity 30. The planar ring 40 preferably serves as a sealing surface within the cavity 30 of the first shaft 26. The frit 44 can be press fit or otherwise received in the planar ring 40. Although depicted as a circular ring, the planar ring 40 can be formed in different shapes, such as oval, rectangular, and other shapes, in various embodiments of the subject invention.

Preferably the frit 44 is inserted into the sealing ring 40 either before or after being filled with secondary particles, according to the first or second embodiments of the subject invention. For example, according to the first preferred embodiment, secondary particles can be filled into a porous support structure, and then sintered to produce a unified structure. Alternatively, according to the second preferred embodiment, secondary particles can be filled into a porous support structure, where the frit 44 is oriented relative to the direction of flow through the chromatography column, i.e., through the chamber 12 and into the frit 44. FIG. 2B depicts a frit 44 according to the first or second embodiments positioned within the sealing ring 40. The frit 44 includes secondary particles 46 impregnated in the frit 44, where the secondary particles 46 preferably penetrate to a depth of greater than about 10 microns in the frit 44. As shown in FIG. 2B, the frit 44 is oriented toward the chamber 12, where the secondary particles 46 are provided in greatest concentration at or near a surface of the frit 44 facing the chamber 12.

Figure 3:
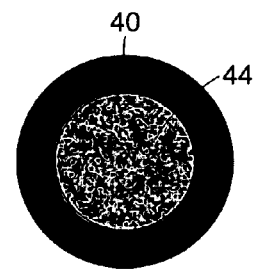
FIG. 3 is a front schematic view of a sealing ring containing a frit configured for use in the HPLC column of FIG. 1.

FIG. 3 is a front view of the circular planar ring 40 and frit 44, after the frit 44 has been inserted into the planar ring 40. As shown in FIG. 3, the frit 44 has been press fit into the planar ring 40, which serves as a sealing surface when the planar ring 40 is installed in the first cavity 30 of the outlet fitting 24. A similar arrangement is provided for the inlet fitting 22 (not shown), which can be configured to receive a frit 44 and planar ring 40.

To assemble an HPLC column, such as that depicted in FIG. 1, a porous support structure, e.g., a sintered stainless steel porous support structure with a media grade ranging from about 0.5 to about 10, is filled with secondary particles to prepare a frit 44, where the secondary particles can be filled either before of after the frit is arranged in a chromatography column. For example, the frit can be made from a 0.5 media grade 316L porous support structure, where the frit 44 is press fit into the sealing ring 40, which is received in the first cavity 30 of the outlet fitting 24. Preferably a top surface of the frit 44 is oriented toward the chamber 12, although orienting is not required when the secondary particles have been sintered. Preferably the second end 16 of the chamber 12 is threaded into the first cavity 30 with sufficient torque to provide a seal capable of withstanding approximately 5,000 to 50,000 psi of pressure.

Figure 7:
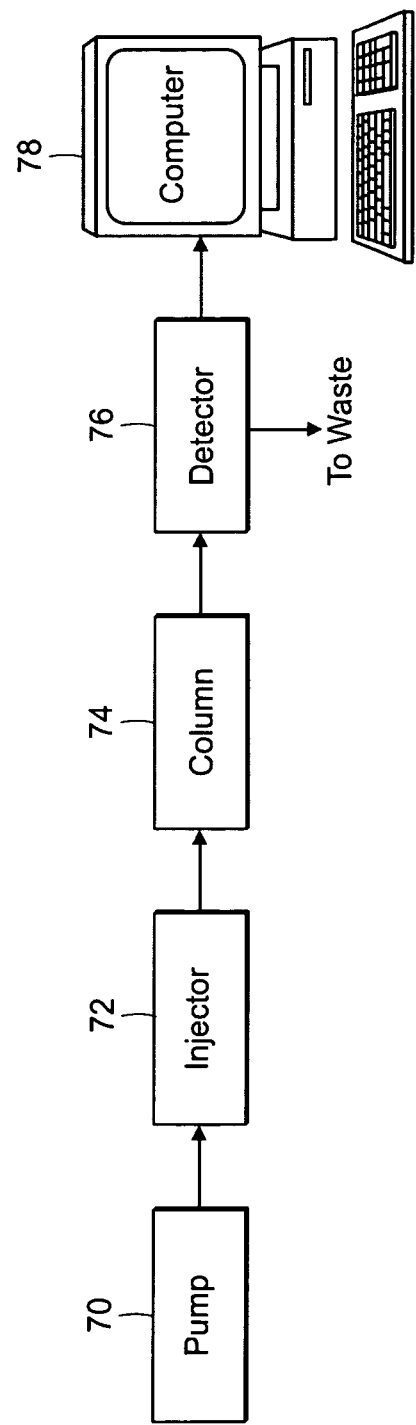
FIG. 7 (PRIOR ART) is a block diagram indicating the components of a typical HPLC system.
Figure 8:
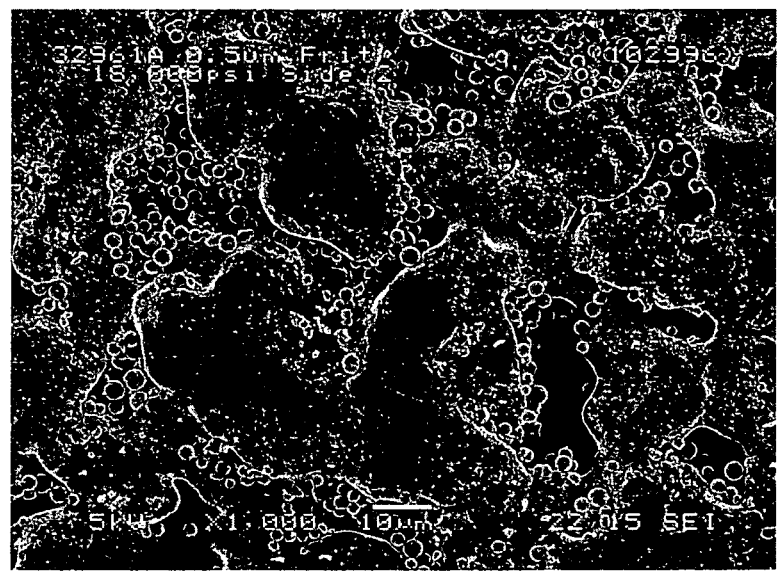
FIG. 8 (PRIOR ART) is a scanning electron micrograph of the downstream side of a conventional 0.5 media grade stainless steel frit removed from a chromatography column packed with 2.2 micron chromatographic packing material.

In a similar manner, a frit can be arranged at an inlet fitting 22 by selecting an appropriate support structure such as a 2.0 media grade 316L porous support structure for the frit 44 to be press fit into the sealing ring 40, which can be received in a cavity of a first shaft of the inlet fitting 22, in the same manner as described above for the outlet fitting 24. Preferably a top surface of the frit 44 is oriented toward the chamber 12, although orienting is not required when the secondary particles have been sintered. The chamber 12 can be filled with a packing material, preferably a chromatographic packing material, using conventional slurry packing techniques. The cavity of the inlet fitting 22 containing the 2.0 media grade frit is then threaded into the first end 14 of the chamber 12 using sufficient torque to provide a seal capable of withstanding approximately 5,000 to 50,000 psi of pressure. The second cavity of the inlet fitting (equivalent to second cavity 32 of the outlet fitting 24) preferably is connected to a solvent stream using a compression screw, ferrule, and tubing, where the tubing typically has a substantially smaller inner diameter than the inner diameter of the chamber 12. The second threaded cavity 32 of the outlet fitting can be connected to a detector (e.g., the detector 76 depicted in FIG. 7) using a compression screw, ferrule, and tubing.

Figure 4A:
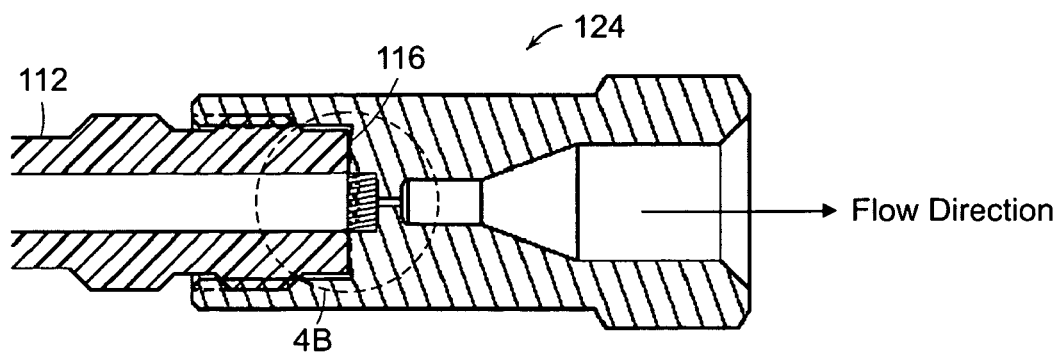
FIG. 4A is an enlarged cross-sectional view of a column outlet of the HPLC column of FIG. 1 according to another arrangement for holding the frit.
Figure 4B:
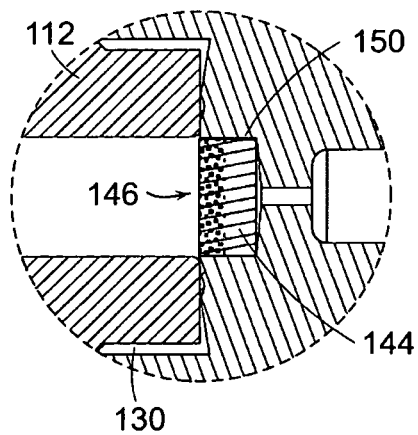
FIG. 4B is an enlargement of the area denoted in FIG. 4A.

Other examples of suitable arrangements for retaining the frit 44 in a chromatographic column are depicted in FIGS. 4A-4B and 5A-5B, where like reference numerals depict similar parts in the following examples. FIGS. 4A and 4B depict an arrangement in which a frit 144 is received in an opening 150 of the outlet fitting 124. Preferably the frit 144 is press fit into the opening 150, although the frit 144 can be otherwise received therein. As shown in FIGS. 4A and 4B, the second end 116 of the chamber 112 contacts an end surface of the outlet fitting 124, either directly or through the use of a bearing. The frit 144 depicted in FIGS. 4A and 4B is the same as the frit 44 of FIGS. 2A and 2B, and is impregnated with secondary particles 146 preferably to a depth of greater than about 10 microns. As shown in FIG. 4B, the frit 144 is oriented toward the chamber 112, although such orienting is not required where the secondary particles 146 are sintered.

Figure 5A:
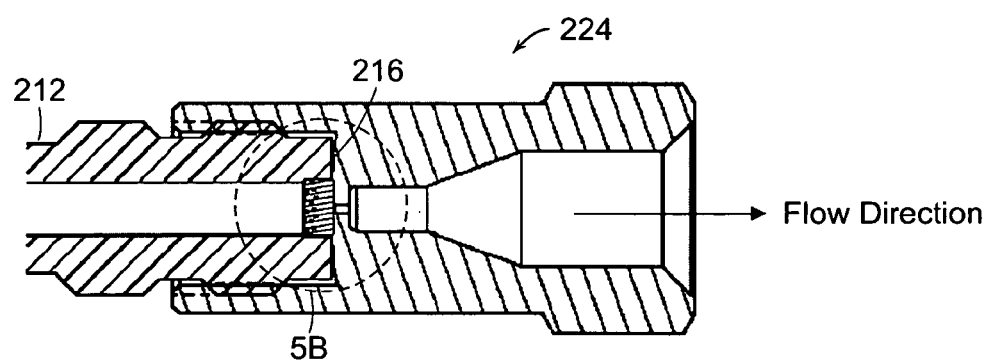
FIG. 5A is an enlarged cross-sectional view of a column outlet of the HPLC column of FIG. 1 according to a further arrangement for holding the frit.
Figure 5B:
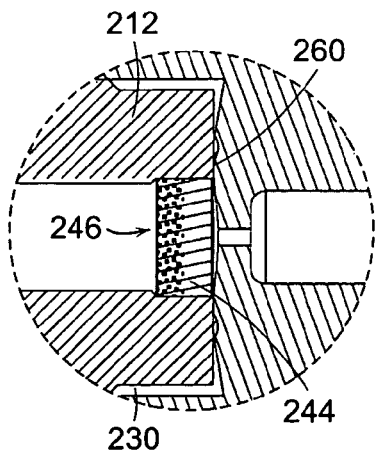
FIG. 5B is an enlargement of the area denoted in FIG. 5A.

FIGS. 5A and 5B depict another arrangement in which a frit 244 is received in an opening 260 located at or near the second end 216 of the chamber 112. Preferably the frit 244 is press fit into the opening 260, although another engagement mechanism can be utilized. The second end 216 of the chamber 212 preferably contacts an end surface of the outlet fitting 224, as in the example of FIGS. 4A and 4B. The frit 244 depicted in FIGS. 5A and 5B is the same as the frit 44 of FIGS. 2A and 2B, and is impregnated with secondary particles 246 preferably to a depth of greater than about 10 microns. As shown in FIG. 5B, the frit 244 is oriented toward the chamber 212, although such orienting is not required where the secondary particles 246 are sintered.

Figure 6A:
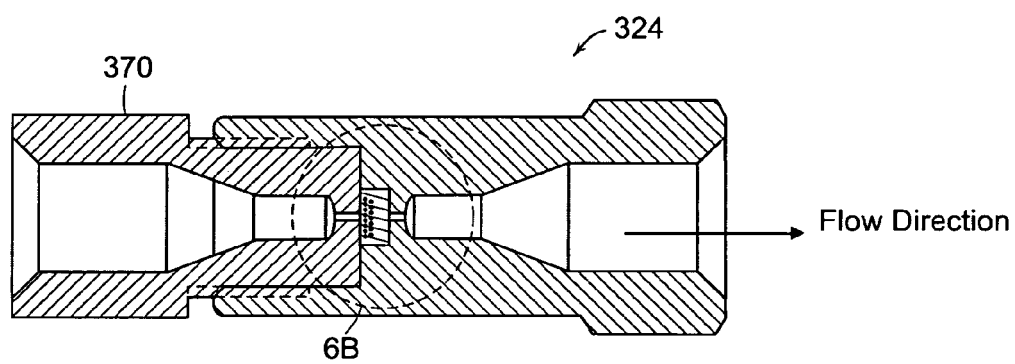
FIG. 6A is a cross-sectional view of a frit arranged as an in-line filter in an HPLC system according to the subject invention.
Figure 6B:
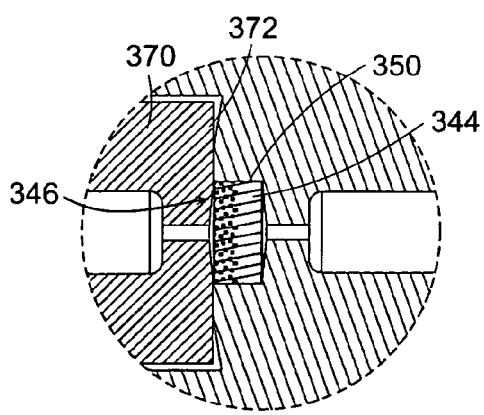
FIG. 6B is an enlargement of the area denoted in FIG. 6A.

FIGS. 6A and 6B depict an arrangement in which a frit 344 is used as an in-line filter in an HPLC system according to the subject invention. The frit 344 is positioned in the HPLC system preferably upstream of the chromatography column, such as between the pump and column, as shown in FIGS. 6A and 6B. Although the in-line filter of FIGS. 6A and 6B can be positioned between the pump and injector, a similar arrangement could be provided between the injector and the column (see, e.g., FIG. 7).

As shown in FIGS. 6A and 6B, first and second complimentary fittings 370 and 324 are connected to a solvent stream in the HPLC system using compression screws, ferrules, and tubing. The frit 344 is press fit into an opening 350 of the first fittiing 370, although another engagement mechanism can be utilized. The fittings 324 and 370 preferably are arranged upstream of the chromatography column, enabling the frit 344 to trap particulate contaminants introduced into the HPLC system prior to reaching the column inlet, thereby prolonging the lifespan of the chromatography column. An end 372 of an first fitting 370 preferably contacts an end surface of the second fitting 324, either directly or through the use of a bearing. The frit 344 depicted in FIGS. 6A and 6B is the same as the frit 44 of FIGS. 2A and 2B, and is impregnated with secondary particles 346 preferably to a depth of greater than about 10 microns. As shown in FIG. 6B, the frit 344 is oriented toward the first fitting 370, so as to retain chromatographic particles upstream, and thereby prevent particle breakthrough, although orienting is not required where the secondary particles 346 of the frit 344 are sintered. Various other arrangements can be provided of a frit of the subject invention for use in an HPLC system that fall within the scope of the subject invention.

EXAMPLE 1

A porous support structure containing 3.5 micron secondary particles was filled as follows. A 0.5 media grade porous support structure was press fit into a circular planar ring (as shown in FIG. 3) that allows for a sealing surface. The sealing ring containing the porous support structure was placed into an outlet fitting. The outlet fitting was attached to an empty second end (outlet end) of a chamber (column). A 3 mL reservoir was attached to the first end (inlet) of the chamber. A tee was attached to the top of the reservoir. A pump was attached to the side opening of the tee. Then, 0.01 grams of 3.5 micron chromatographic packing materials was admixed and sonicated in 3 mL tetrahydrofuran (THF). The particle-solution was sonicated for 2 minutes. The particle-solution was poured or pipetted into the reservoir through the top opening of the tee. The particle-solution was topped off with approximately 2.2 mL of THF. The top opening in the tee, used to introduce the solutions, was plugged. A pressure of 6,000 psi, delivered by the pump, was applied until 5 mL had been collected at the chamber outlet. The outlet fitting assembly was separated from the chamber. The sealing ring containing the particle filled porous support structure was removed from the outlet fitting assembly. Excess material was removed from the top surfaces of the sealing ring and filled porous support structure. The same procedure was used to fill a frit with 2 micron chromatographic particles as shown in FIG. 10C.

Example 1 is particularly suitable for preparing frits for use at the outlet side of the column without requiring a secondary sintering step. According to this embodiment of the subject invention, the frit is oriented with respect to a direction of flow through a chromatography column, so as to prevent fluid forces from washing the secondary particles out of the frit.

EXAMPLE 2

Frits containing 4 micron stainless steel particles were prepared as follows. A porous support structure (2.0 media grade sintered stainless steel) having a diameter of 2.1 mm and a thickness of 0.040 in. was press fit into a stainless steel sealing ring. The porous support structure was placed in a fixture whereby vacuum was drawn through the porous support structure. Narrowly sized particles (4 microns in diameter) were suspended in 10 mL toluene and mixed using a magnetic stir bar. A small volume of particle suspension was placed on the porous support structure and allowed to penetrate and pack into the void spaces within the support structure. The filled frit was wiped clean of excess particles and then sintered to 1900° F. for approximately one hour in a controlled $H_2$ atmosphere to permanently immobilize the particles into a unified structure. Both 0.5 and 2.0 media grade frits were filled according to this process.

In Example 2, the described embodiment includes a "second" step of sintering the secondary particles received in the porous support structure.

EXAMPLE 3

In the above examples, each of the frits preferably has a density of at least 50%. In other words, the void spaces or pores make up less than 50% by volume of the frits. The density of the frits increases after secondary particles are filled in the void spaces, thereby decreasing porosity.

In Example 3, depth of penetration was measured using 0.5 and 2.0 media grade porous support structures. For the 2.0 media grade porous support structure, the porosity of the unfilled structure was 32% (68% dense). For the 0.5 media grade porous support structure, the porosity of the unfilled structure was 19% (81% dense). Each support structure had a diameter of 2 inches and a thickness of 0.125 inches. Porosity was measured by comparing the weight of the porous support structure to the expected weight of a solid part of 316L stainless steel. Then, the porous support structures were slurry filled from one side with 4 micron stainless steel spherical particles (secondary particles) and dried to obtain a new weight. Assuming about 50% of the penetrated volume of void spaces in the porous support structure is filled with secondary particles, the depth of penetration of the secondary particles into the void spaces can be calculated.

As expected, the depth of penetration of secondary particles in the 2.0 media grade support structures was greater than in the 0.5 media grade support structures. In both support structures, the unfilled and filled porosity of the frits was low (less than 50% by volume), as a result of the high density of these structures. The penetration of the secondary particles in the 2 media grade frit was approximately 0.007 inches (178 microns). For the 0.5 media grade frit, the penetration of secondary particles was approximately 0.0011 inches (28 microns).

EXAMPLE 4

Figure 9:
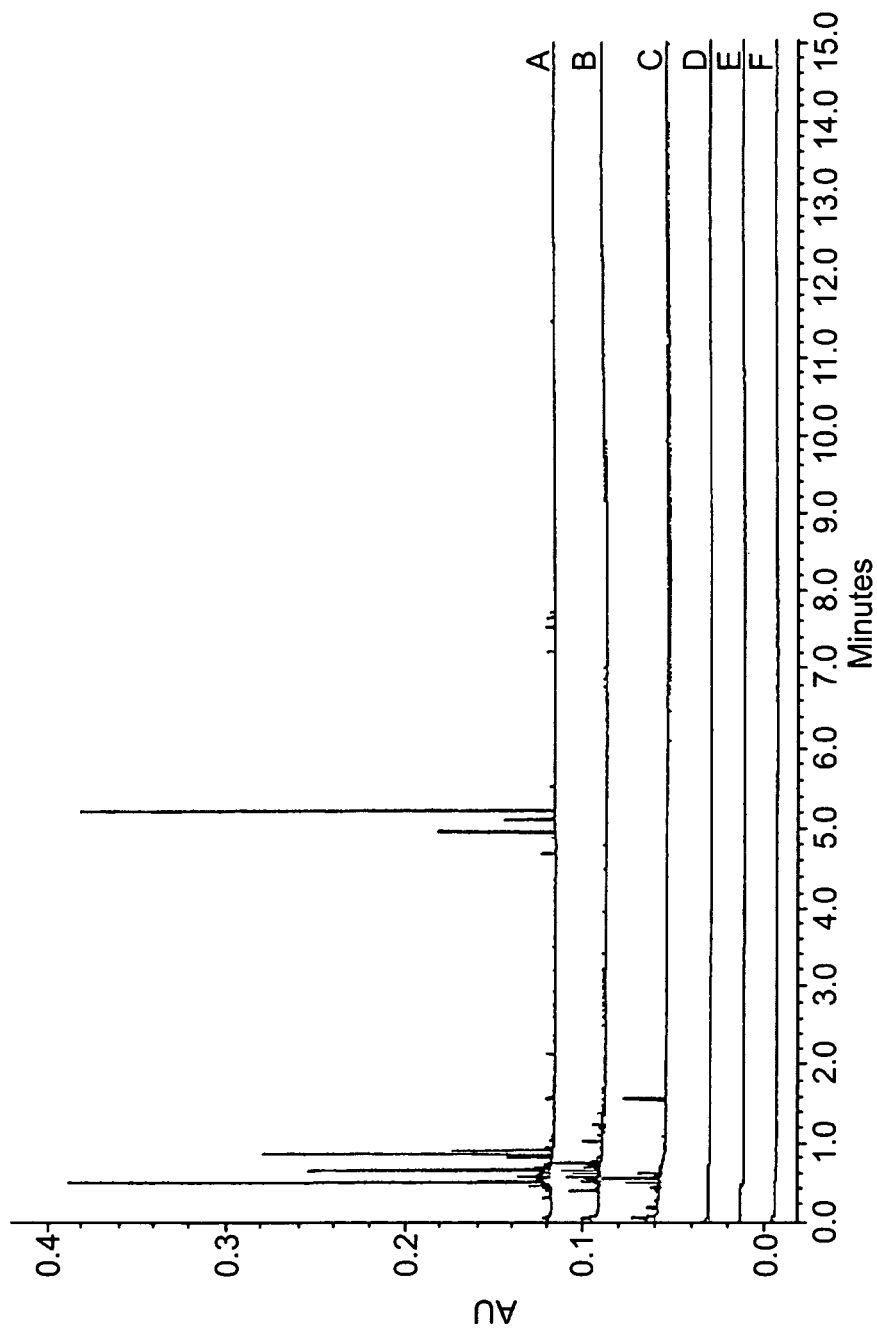
FIG. 9 is a graph having a series of UV traces for six columns, where columns A-C used conventional 0.5 media grade frits, and columns D-F used frits filled with secondary particles according to the subject invention.

Six columns (A-F) were packed with 1.7 micron chromatographic packing material, where a 0.5 media grade frit was arranged in each column. As discussed earlier, columns A-C used conventional 0.5 media grade frits at the column outlet, whereas columns D-F used 0.5 media grade frits filled with secondary particles. The frits used in columns D-F were filled using 3.5 micron secondary particles of the same composition as the packing material, according to the method described in Example 1. FIG. 9 shows the UV traces collected at 254 nm during column equilibration in the HPLC mobile phase. The UV traces for columns A-C clearly show spikes that are indicative of the migration of the 1.7 micron packing material through the conventional frits. No spikes are present in UV traces for columns D-F assembled using the prefilled frits of the invention at the outlet.

Figure 10A:
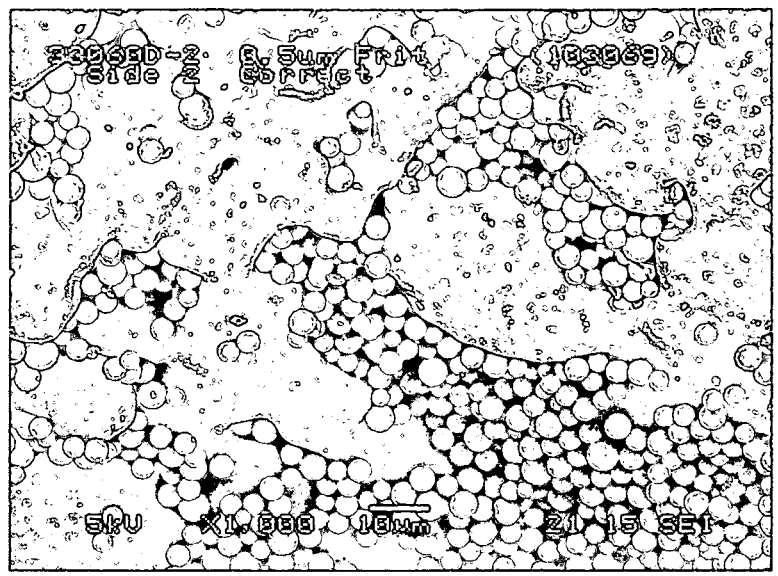
FIG. 10A is a scanning electron micrograph of the top of a 0.5 media grade frit filled with 3.5 micron chromatographic particles.
Figure 10B:
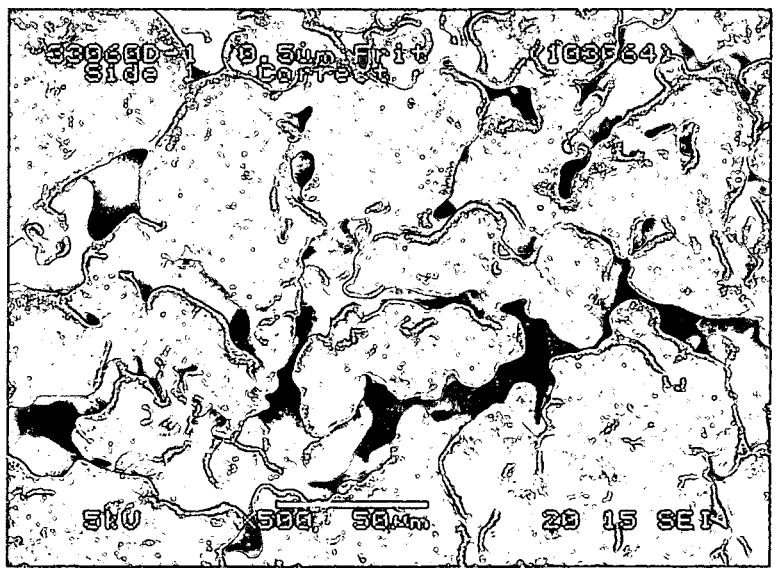
FIG. 10B is a scanning electron micrograph of the bottom of a 0.5 media grade frit filled with 3.5 micron chromatographic particles.
Figure 10C:
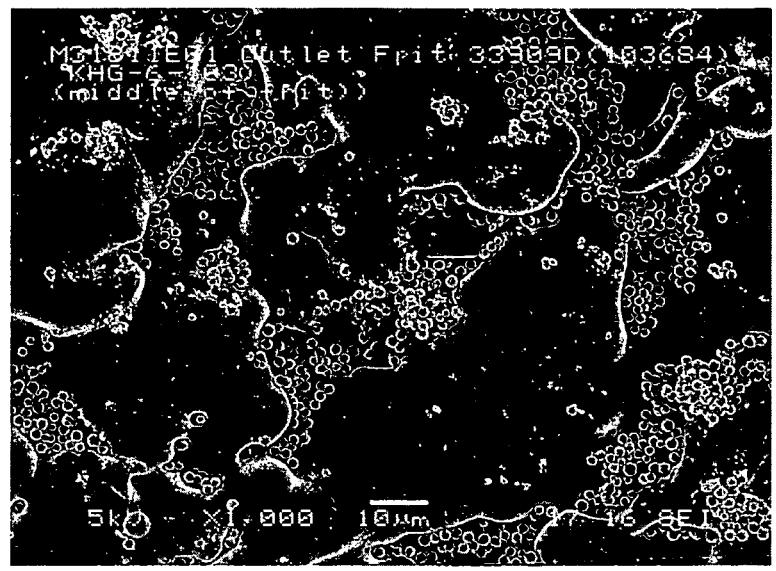
FIG. 10C is a scanning electron micrograph of the top of a 0.5 media grade frit filled with 2 micron chromatographic particles.

As shown in FIG. 10(A), when the 0.5 media grade frit is filled with 3.5 micron secondary particles, the secondary particles become impregnated in the void spaces, thereby forming a secondary pore network. As shown in the bottom view of FIG. 10(B), the secondary particles have become embedded within the void spaces or pores of the frit, and there is no evidence of particle breakthrough.

Figure 11A:
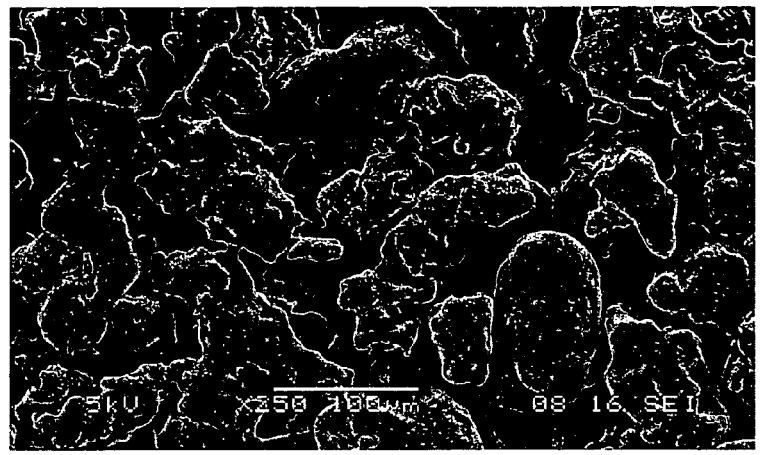
FIG. 11A is a scanning electron micrograph of the top of a 0.5 media grade frit prior to filling.
Figure 11B:
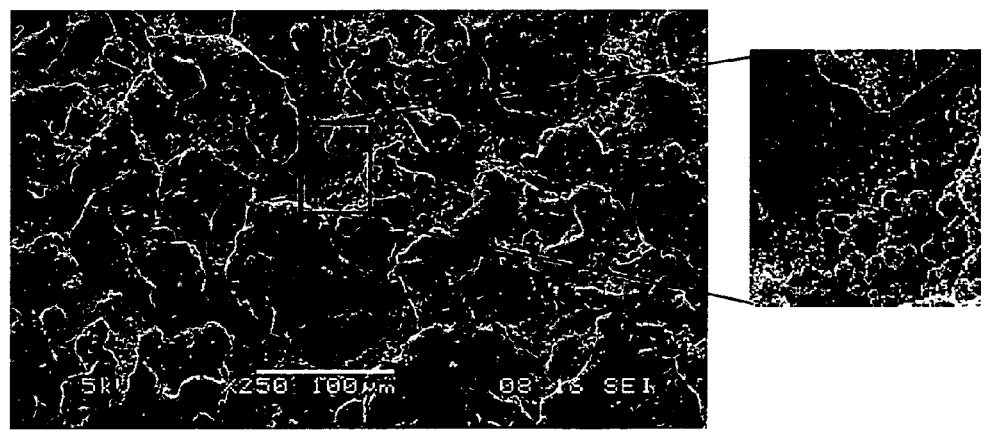
FIG. 11B is a scanning electron micrograph of the top of a 0.5 media grade frit after filling with 4 micron stainless steel particles and sintering in a secondary process.

FIG. 11(A) is a SEM of a 0.5 media grade frit prior to being filled with secondary particles. As shown in FIG. 11(B), after filling with 4 micron spherical stainless steel particles and being sintered in a secondary sintering step, a unified structure is formed.

Although the disclosed frits, chromatography columns, and related methods and apparatus have been described with respect to preferred embodiments, it is apparent that modifications and changes can be made thereto without departing from the spirit and scope of the invention as defined by the appended claims.

Incorporation by Reference

The entire contents of all patents, published patent applications and other references cited herein are hereby expressly incorporated herein in their entireties by reference.

What is claimed is

1. A frit comprising:
    a porous support structure produced from sintered irregularly shaped powder particles about 45 to 100 micrometers in size, the porous support structure having a media grade between about 0.5 and about 10, and defining a plurality of void spaces; and
    a plurality of spherical particles no more than about 5 micrometers in size sintered within the porous support structure to each other, to the porous support structure surrounding the void spaces, or both, the spherical particles defining a secondary pore network within the void spaces sufficient to retain packing materials with diameters of less than about 2.5 microns within the frit,
    wherein the void spaces are filled with the plurality of spherical particles such that the frit has a density of at least 50% by volume.

2. The frit of claim 1, wherein the void spaces are partially filled with the particles.

3. The frit of claim 1, wherein the packing materials are chromatographic packing materials.

4. The frit of claim 1, wherein the porous support structure comprises a material selected from the group consisting of metals, metal alloys, metal oxides, ceramics, and polymers.

5. The frit of claim 1, wherein the porous support structure comprises a material selected from the group consisting of sinterable metals, sinterable metal alloys, sinterable metal oxides, sinterable ceramics, and sinterable polymers.

6. The frit of claim 1, wherein the porous support structure comprises a material selected from the group consisting of stainless steel, titanium, PEEK, polyethylene, polypropylene, synthetic resinous fluorine-containing polymers glass, silica, titania, and zirconia.

7. The frit of claim 1, wherein the porous support structure comprises stainless steel.

8. The frit of claim 1, wherein the porous support structure comprises 316 stainless steel.

9. The frit of claim 1, wherein the spherical particles range from about 3 microns to about 5 microns in diameter.

10. The frit of claim 1, wherein the spherical particles are about 3.5 microns in diameter.

11. The frit of claim 10, wherein the spherical particles are about 4 microns in diameter.

12. The frit of claim 1, wherein the spherical particles have the same composition as the porous support structure.

13. The frit of claim 1, wherein the spherical particles have a different composition than the porous support structure.

14. The frit of claim 1, wherein the spherical particles are spherical stainless steel particles.

15. The frit of claim 1 for use in a chromatography column.

16. The frit of claim 15, wherein the chromatography column is a high pressure liquid chromatography (HPLC) column.

17. The frit of claim 16, wherein the chromatography column is a high pressure liquid chromatography column packed with chromatographic packing materials with particle diameters of less than about 2.5 microns.

18. The frit of claim 1, wherein the particles fill the void spaces of the porous support structure to a depth of greater than about 10 microns.

19. The frit of claim 15, wherein the chromatography column is packed with chromatographic packing materials.

20. The frit of claim 19, wherein the chromatographic packing materials are selected from the group consisting of silica gel, derivatized silica gel, zirconia, derivatized zirconia, titanium oxide, derivatized titanium oxide, organo-silica hybrids, derivatized organo-silica hybrids, hybrids of metal oxides, and derivatized hybrids of metal oxides.

21. A frit configured to be received in a tubular chamber, the frit comprising:
    a porous support structure produced from sintered irregularly shaped powder particles about 45 to 100 micrometers in size, the porous support structure having a media grade between about 0.5 and about 10, and defining a plurality of void spaces; and
    a plurality of spherical particles sintered within the porous support structure to each other, to the porous support structure surrounding the void spaces, or both,
    wherein the void spaces are partially filled with the plurality of spherical particles, and the spherical particles are dimensioned with respect to the void spaces to retain chromatographic packing materials with diameters of less than about 2.5 microns.

* * * * *